(12) United States Patent
Perrotto et al.

(10) Patent No.: US 8,865,225 B2
(45) Date of Patent: Oct. 21, 2014

(54) COMPOSITION COMPRISING A SOLID STATE HYPOTHIOCYANITE SALT OF A CATION

(71) Applicant: Alaxia SAS, Lyons (FR)

(72) Inventors: Sandrine Perrotto, Fleurieu sur l'arbresle (FR); Sébastien Gluszok, Givenchy en Gohelle (FR); Philippe Bordeau, St Pierre de chandieu (FR)

(73) Assignee: Alaxia SAS, Lyons (FR)

( * ) Notice: Subject to any disclaimer, the term of this patent is extended or adjusted under 35 U.S.C. 154(b) by 181 days.

(21) Appl. No.: 13/648,365

(22) Filed: Oct. 10, 2012

(65) Prior Publication Data

US 2013/0089620 A1    Apr. 11, 2013

Related U.S. Application Data

(60) Provisional application No. 61/545,691, filed on Oct. 11, 2011.

(30) Foreign Application Priority Data

Oct. 10, 2011 (FR) .................................. 11 59138

(51) Int. Cl.
*A61K 33/00* (2006.01)
*A61K 45/06* (2006.01)
*A61K 33/04* (2006.01)

(52) U.S. Cl.
CPC .................. *A61K 45/06* (2013.01); *A61K 33/04* (2013.01)
USPC ............................ 424/611; 424/607; 424/610

(58) Field of Classification Search
None
See application file for complete search history.

(56) References Cited

U.S. PATENT DOCUMENTS

| | | | |
|---|---|---|---|
| 8,263,138 B2 * | 9/2012 | Perraudin | 424/661 |
| 2004/0156917 A1 | 8/2004 | Conner | 424/616 |
| 2006/0018817 A1 | 1/2006 | Ashby | 423/366 |
| 2009/0246146 A1 | 10/2009 | Banfi et al. | 424/43 |
| 2009/0317378 A1 * | 12/2009 | Perraudin | 424/130.1 |

FOREIGN PATENT DOCUMENTS

| | | | | |
|---|---|---|---|---|
| WO | WO 02/097076 | | 12/2002 | ............... C12N 9/08 |
| WO | WO 2007/134180 | | 11/2007 | ............. B26B 13/12 |
| WO | WO 2008/003688 | * | 1/2008 | ............. A61K 38/40 |
| WO | WO 2008/045696 | | 4/2008 | ............. A61K 38/44 |
| WO | WO 2010/086530 | | 8/2010 | ............. A61K 38/40 |
| WO | WO 2010/086531 | | 8/2010 | ................ A61J 1/20 |

OTHER PUBLICATIONS

Singh et al.; "Inhibition of Lactoperoxidase by Its Own Catalytic Product: Crystal Structure of the Hypothiocyanate-Inhibited Bovine Lactoperoxidase at 2.3-ÅResolution"; Biophysical Journal; vol. 96, (Jan. 2009); pp. 646-654.*

International Search Report and Written Opinion dated Nov. 19, 2012 issued in PCT Application No. PCT/EP2012/070092 with English Translation.

International Search Report for FR 1159138 with mail date of Mar. 21, 2012.

Pollock, J., et al. (1992) "Lactoperoxidase-catalyzed oxidation of thiocyanate ion: a carbon-13 nuclear magnetic resonance study of the oxidation products" Biochimica et Biophysica Acta, 1159:279-285.

* cited by examiner

Primary Examiner — Jeffrey T Palenik
(74) Attorney, Agent, or Firm — Harness, Dickey & Pierce, P.L.C.

(57) ABSTRACT

A solid composition is provided herein comprising at least one hypothiocyanite salt (OSCN—) of a cation in an amorphous and/or crystalline powder form. Also provided herein are methods of making the composition and methods of treating various conditions, such as airborne infection, lower respiratory tract infection or upper respiratory tract infection.

24 Claims, No Drawings

COMPOSITION COMPRISING A SOLID STATE HYPOTHIOCYANITE SALT OF A CATION

CROSS-REFERENCE TO RELATED APPLICATIONS

This application claims the benefit and priority under 35 U.S.C. §119 to French Application No. 11/59138 filed on 10 Oct. 2011 and to U.S. Provisional Application No. 61/545, 691 filed on 11 Oct. 2011. The contents of each application recited above are incorporated herein by reference in their entirety.

FIELD

The present invention generally relates to a solid composition comprising at least one hypothiocyanite salt (OSCN—) of a cation in an amorphous and/or crystalline powder form. The present invention also generally relates to methods of making the composition and methods of treating various conditions, such as airborne infection, lower respiratory tract infection and/or upper respiratory tract infection.

BACKGROUND

The interest of hypothiocyanite ions is no longer to be shown for either the agri-food industry or for the pharmaceutical industry.

The hypohalite and/or hypothiocyanite ion is generated in vivo in a solution by the lactoperoxidase system according to the following equation:

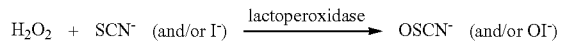

The pharmacological properties of the hypothiocyanite ion are known, namely, its biocide properties, but due to the instability of this chemical species, uses are delicate, complicated and limited.

By reason of this instability, the lactoperoxidase system was at the origin often delivered complete in powder form which permitted to generate in situ the OSCN— ion by triggering the reaction, for instance, by placing it in a solution.

According to the uses, the oxygen donor could be a percarbonate, the glucose/glucose oxidase system or even $H_2O_2$.

The lactoperoxidase system is used for instance in cosmetic products such as toothpastes marketed by the Laclede company under the name of Biotene®.

More recently, one has observed the appearance of patent applications for the use of the lactoperoxidase system in human health. For instance, there is application WO2008/045696 regarding a method of usage and its compounds for the treatment of vaginal disorders. One can also mention methods and compositions to treat pulmonary problems (US 2004/0156917 and WO2007/134180).

Variants with possible substitution of the thiocyanate pseudohalogen by iodine (US 2009/0246146) in combination or not with the enzyme have also been proposed.

All applications described use either the in situ production by administration of the complete system and/or a part of the system with the use of one of the components present in situ.

A step has been cleared with the appearance at the beginning of the years 2000 (WO2002/097076) of a process that permits to produce OSCN— and/or OI— agents with separation of the enzyme precursors through the use of coagulant agents which led to the production of OSCN— and/or OI— in large volume solutions.

From WO2010/086531, one is aware of materials which enable to produce, extemporaneously, as needed, a solution comprising OSCN— or OI—.

SUMMARY

This section provides a general summary of the disclosure, and is not a comprehensive disclosure of its full scope or all of its features.

The inventors have recognized that one of the major problems of using the afore-mentioned active ingredient is the impossibility of storing over a long period of time in accordance with the requirements of the Pharmaceutical Regulations leading to its extemporaneous production, which if mastered, only poses the problem of using dedicated systems but which can nevertheless be an obstacle for its use.

Embodiments of the present invention permits obtaining a composition that comprises a solid state hypothiocyanite salt of a cation, in powder form.

In one embodiment, a solid composition is provided that comprises at least a hypothiocyanite salt (OSCN—) of a cation, in the form of an amorphous and/or crystalline powder in a percentage by weight ranging between 0.01% and 10%.

In another embodiment, a process for producing the composition according to the invention is provided herein, wherein the following steps are applied to an aqueous solution containing at least a hypothiocyanite ion (OSCN—):

a) To said aqueous solution, at least one alcohol is added ranging between about 10 and about 99.9% by weight, with this alcohol being a dissolved solid or a solvent;

b) The temperature is set;

c) The solvent is removed; and d) A composition in solid form is obtained.

In another embodiment, various methods of using the composition described herein, alone or in combination with other antimicrobial, preservative or antibiotic agents are provided. For example, for the treatment of airborne infections; lower or upper respiratory tract infections; gastric infections; cuts; cystic fibrosis; COPD. Further examples are for treating care materials and medical devices, and for water and air treatment.

Further areas of applicability will become apparent from the description provided herein.

DETAILED DESCRIPTION

In one embodiment, a solid composition is provided comprising at least a hypothiocyanite salt (OSCN—) of a cation, in the form of an amorphous and/or crystalline powder in a percentage by weight ranging between 0.01% and 10%.

According to an embodiment, the composition also contains a thiocyanate ion salt (SCN—) in a percentage by weight ranging between 0.1% and 10%.

According to an embodiment, the composition may also contain gluconic acid in a percentage by weight ranging between 0.01% and 10%.

According to an embodiment, the composition may also contain a phosphate or carbonate salt of an alkaline cation in a percentage by weight ranging between 10 and 99.9%.

According to an embodiment, the composition may also contain glucose.

According to an embodiment, the cation is chosen among alkaline cations, such as sodium and potassium, or among the group made up of calcium or magnesium.

In another embodiment, a solution is provided comprising a composition as described herein which is solubilized in a hydroalcoholic solution, of which alcohol represents 0.01% to 100 by weight of the solvent.

According to an embodiment, the alcohol is chosen among ethanol, polyethylene glycol, tert-butanol or compounds carrying hydroxyl functions chosen among the group made up by mannitol, trehalose and lactose.

According to an embodiment, the alcohol is ethanol in a proportion by weight ranging between 10 and 99.9%.

According to an embodiment, the alcohol is polyethylene glycol (PEG) in a proportion by weight ranging between 10 and 50%.

According to an embodiment, the dissolved alcohol is mannitol in a proportion by weight ranging between 0.1 and 2 g.l-1(=0.01 to 0.2%).

According to an embodiment, the dissolved alcohol is trehalose in a proportion by weight ranging between 0.1 and 15 g.l-1(=0.01 to 1.5%).

According to an embodiment, the dissolved alcohol is lactose in a proportion by weight ranging between 0.01 and 2 g.l-1(=0.01 to 0.2%).

In one embodiment, the composition comprising a hypothiocyanite ion (OSCN—) is stable over a minimum period of 2 months and up to 6 months.

In one embodiment, the composition comprising a hypothiocyanite ion (OSCN—) is stable over a minimum period of 2 months and up to 4 months.

In one embodiment, the composition is kept at a temperature between 0° C. and −100° C.

In one embodiment, the composition is kept at a temperature between −20° C. and −80° C.

In another embodiment, a process for producing a composition described herein is provided, wherein the following steps are applied to an aqueous solution containing at least a hypothiocyanite ion (OSCN—):

a) To said aqueous solution, at least one alcohol is added ranging between about 10 and about 99.9% by weight, with this alcohol being a dissolved solid or a solvent;
b) The temperature is set;
c) The solvent is removed; and
d) A composition in solid form is obtained.

According to an embodiment of the process, the alcohol is chosen among ethanol, polyethylene glycol, tert-butanol, or compounds carrying hydroxyl functions such as mannitol, trehalose and lactose.

According to an embodiment of the process, an association of at least two of said alcohols is added to the aqueous solution.

According to an embodiment of the process, the alcohol is ethanol, in a proportion by weight ranging between about 10 and 99.9%.

According to an embodiment of the process, the alcohol is glycerol, in a proportion by weight ranging between about 10 and about 50%.

According to an embodiment of the process, the alcohol is polyethylene glycol (PEG), in a proportion by weight ranging between about 10 and about 50%.

According to an embodiment of the process, the alcohol is mannitol, in a proportion by weight ranging between about 0.1 and about 2 g.l-1(=0.01 to 0.2%).

According to an embodiment of the process, the alcohol is trehalose, in a proportion by weight ranging between about 0.1 and about 15 g.l-1(=0.01 to 1.5%).

According to an embodiment of the process, the alcohol is lactose, in a proportion by weight ranging between about 0.1 and about 2 g.l-1(=0.01 to 0.2%).

According to an embodiment of the process, the temperature is set between about zero ° C. and about −100° C.

According to an embodiment of the process, the temperature is set between about −10° C. and about −80° C.

According to an embodiment of the process, the temperature is set at about −20° C.

According to an embodiment of the process, the temperature is set at about −80° C.

According to an embodiment of the process, the solvents are removed substantially simultaneously.

According to an embodiment of the process, the solvents are removed consecutively.

According to an embodiment of the process, the water is removed first.

According to an embodiment of the process, the solvents are removed by evaporation in the form of an azeotrope, at reduced pressure.

According to an embodiment of the process, evaporation takes place at a temperature between about 35° C. and about 45° C.

According to an embodiment of the process, evaporation takes place at ambient temperature.

According to an embodiment of the process, evaporation takes place at a low temperature, namely, below about 80° C.

According to an embodiment of the process, evaporation takes place at reduced pressure.

According to an embodiment of the process, the solvent(s) is/are removed by lyophilization.

According to an embodiment of the process, the solvents are removed at a temperature between about 4° C. and about 60° C.

According to an embodiment of the process, the process comprises, in addition before step a), a step x) for the production of the aqueous solution containing the hypothiocyanite ion (OSCN—) by placing in contact a peroxidase, a pseudohalogen and an oxygen donor.

According to an embodiment of the process, the peroxidase is lactoperoxidase, the pseudo-halogen is the thiocyanate ion (SCN—), the oxygen donor is chosen from the group made up by hydrogen peroxide, percarbonate and the glucose/glucose oxidase pair.

According to an embodiment of the process, the aqueous solution is buffered and the pH falls within the [6; 11] range.

According to an embodiment of the process, the aqueous solution is buffered by a phosphate buffer for which the concentration falls between about 50 mM and about 200 mM.

According to an embodiment of the process, the aqueous solution is buffered by a carbonate buffer for which the concentration falls between about 50 mM and about 1 M.

According to an embodiment of the process, the aqueous solution is obtained by enzyme production according to the two successive enzyme reactions below:

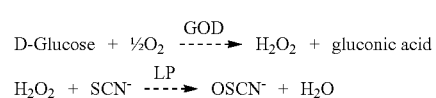

where GOD is glucose oxidase; $H_2O_2$, hydrogen peroxide; LP the lactoperoxidase; $SCN^-$ the ion thiocyanate and $OSCN^-$ the hypothiocyanite ion.

According to an embodiment of the process, the process can further comprise, between steps x) and step a), a filtration step y) on a membrane for which the cutting threshold is less than or equal to ≤30 kDa.

According to an embodiment of the process, the membrane has a cutting threshold of about 10 kDa.

According to an embodiment of the process, the aqueous solution available also contains glucose.

According to an embodiment of the process, the aqueous solution available also contains gluconic acid.

According to an embodiment of the process, the aqueous solution available also contains the thiocyanate ion.

According to an embodiment of the process, the aqueous solution available is buffered.

According to an embodiment of the process, the pH of the aqueous solution available falls within the [6; 11] range.

According to an embodiment of the process, the aqueous solution available is buffered by a phosphate buffer ranging between about 50 mM and about 200 mM.

According to an embodiment of the process, the aqueous solution available is buffered by a carbonate buffer ranging between about 50 mM and about 1M.

According to an embodiment of the process, the OSCN— ion of said aqueous solution is obtained by electrolysis.

According to an embodiment of the process, the OSCN— ion of said aqueous solution is obtained by synthesis.

According to an embodiment of the process, the solid form composition obtained at step d) is a powder.

According to an embodiment of the process, the powder obtained is amorphous.

According to an embodiment of the process, the powder obtained is partially crystaline.

According to an embodiment of the process, the powder obtained is crystaline.

In another embodiment, the use of a composition described herein, alone or in combination with other antimicrobial, preservative or antibiotic agents, is provided for the treatment of airborne infections, for lower respiratory tract infections, or for upper respiratory tract infections.

In another embodiment, the use of a composition described herein, alone or in combination with other antimicrobial, preservative or antibiotic agents, is provided for the treatment of gastric infections, cuts, infection in a mucous membrane or skin.

In another embodiment, the use of a composition described herein, alone or in combination with other antimicrobial, preservative or antibiotic agents, is provided for the treatment of cystic fibrosis and COPD.

Alternatively or additionally, a method for treating a condition selected from the group consisting of an airborne infection, a lower respiratory tract infection, an upper respiratory tract infection, a gastric infection, a cut, an infection in a mucous membrane or skin, cystic fibrosis and COPD in a subject in need thereof is provided herein. The method comprises administering to the subject a composition as described herein, alone or in combination with another antimicrobial, preservative or antibiotic agent, in a therapeutically effective amount.

In another embodiment, the use of a composition described herein, alone or in combination with other antimicrobial, preservative or antibiotic agents, is by the direct use of the powder or after its resolubilization.

In another embodiment, the use of a composition described herein, alone or in combination with other antimicrobial, preservative or antibiotic agents, is provided for the treatment of care materials and medical devices.

In another embodiment, the use of a composition described herein, alone or in combination with other antimicrobial, preservative or antibiotic agents, is for topical application.

In another embodiment, the use of a composition described herein, alone or in combination with other antimicrobial, preservative or antibiotic agents, is by injection.

In another embodiment, the use of a composition described herein, alone or in combination with other antimicrobial, preservative or antibiotic agents, is provided for air treatment by decontaminating the air (passive), environmental decontamination (active) and/or environmental cleanup.

In another embodiment, the use of a composition described herein, alone or in combination with other antimicrobial, preservative or antibiotic agents, is provided for the treatment of drinking water, recreational water and waters used for subsequent antimicrobial applications.

In another embodiment, the use of a composition described herein, alone or in combination with other antimicrobial, preservative or antibiotic agents for the use or preservation of cosmetics.

In another embodiment, the use of a composition described herein, alone or in combination with other antimicrobial, preservative or antibiotic agents, is provided for the treatment of materials and equipment.

In another embodiment, the use of a composition described herein, alone or in combination with other antimicrobial, preservative or antibiotic agents, is for the treatment of packaging materials.

In another embodiment, the use of a composition described herein, alone or in combination with other antimicrobial, preservative or antibiotic agents, is provided for the treatment of textiles.

In another embodiment, the use of a composition described herein, alone or in combination with other antimicrobial, preservative or antibiotic agents, is provided for the treatment of plants.

In another embodiment, the use of a composition described herein, alone or in combination with other antimicrobial, preservative or antibiotic agents, is provided for the treatment of soils.

In another embodiment, the use of a composition described herein, alone or in combination with other antimicrobial, preservative or antibiotic agents, is provided for co-use with cleaning and disinfecting agents.

EXAMPLES

The following examples are merely illustrative, and do not limit this disclosure in any way.

Example 1

OSCN— Enzyme Production According to Two Successive Enzyme Reactions

Enzyme production following the two successive enzyme reactions below:

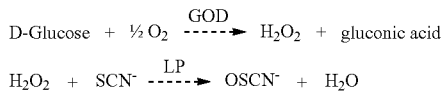

wherein GOD: Glucose Oxidase; $H_2O_2$: Hydrogen peroxide; LP : Lactoperoxidase; SCN—: Thiocyanate; OSCN—: hypothiocyanite ion.

To a solution of water (100 ml), a 50 mM carbonate buffer and containing 0.4 g of D-glucose and 0.04 g of GOD, 0.12 g of LP are added 1 ml of a 2 M sodium thiocyanate solution (NaSCN). The solution is stirred at ambient temperature at 200 rpm for 10 minutes. The pH of the solution is 9.2.

After reaction, the solution is filtered over a 10 kDa ultrafiltration membrane. A solution is obtained containing:

$H_2O + glucose + gluconic\ acid + OSCN^- + SCN^- + Na^+$

The OSCN$^-$ concentration obtained is 1340 μM.

Example 2

OSCN$^-$ in a Hydroalcoholic Solution

To a diluted solution obtained according to Example 1, with an OSCN$^-$ concentration of 520 μM are added 20% by weight of absolute ethanol. The temperature is then lowered to −30° C. The solution freezes. An OSCN$^-$ ion concentration of 510 μM is measured after a period of 1 month as well as 495 μM after a period of 2 months. The difference observed is due to the precision of the measuring method (spectrophotometry).

Example 3

OSCN$^-$ in a Hydroalcoholic Solution

To a diluted solution obtained according to Example 1, with an OSCN$^-$ concentration of 450 μM, 20% by weight of absolute ethanol is added. The temperature is lowered to −30° C. The solution freezes. An OSCN$^-$ ion concentration of 470 μM is measured after a period of 1 month as well as 440 μM after a period of 2 months. The difference observed is due to the precision of the measuring method (spectrophotometry).

Example 4

OSCN$^-$ in a Hydroalcoholic Solution

To a diluted solution obtained according to Example 1, with an OSCN$^-$ concentration of 510 μM, 50% by weight of absolute ethanol is added. The temperature is lowered to −30° C. The solution freezes. An OSCN$^-$ ion concentration of 530 μM is measured after a period of 1 month as well as 490 μM after a period of 2 months. The difference observed is due to the precision of the measuring method (spectrophotometry).

Example 5

OSCN$^-$ in a Hydroalcoholic Solution

The same solution used according to Example 4, with an OSCN$^-$ concentration of 510 μM, is preserved at a temperature of −80° C. The solution freezes. An OSCN$^-$ ion concentration of 480 μM is measured after a period of 1 month as well as 500 μM after a period of 2 months. The difference observed is due to the precision of the measuring method (spectrophotometry).

Example 6

OSCN$^-$ in a Hydroalcoholic Solution

The same solution used according to Example 4, with an OSCN$^-$ concentration of 510 μM, is preserved at a temperature of −80° C. The solution freezes. An OSCN$^-$ ion concentration of 520 μM is measured after a period of 1 month as well as 490 μM after a period of 2 months. The difference observed is due to the precision of the measuring method (spectrophotometry).

The results observed in Examples 2 to 7 are assembled in Table 1:

TABLE 1

| | OSCN$^-$ in a hydroalcoholic solution | | | | |
|---|---|---|---|---|---|
| Example no. | Quantity of alcohol in % by weight | Conservation temperature | [OSCN$^-$] at T = 0 in μM | [OSCN$^-$] at T = 1 month μM | [OSCN$^-$] at T = 2 months in μM |
| Example 2 | 20 | −30° C. | 520 | 510 | 495 |
| Example 3 | 20 | −30° C. | 450 | 470 | 440 |
| Example 4 | 50 | −30° C. | 510 | 530 | 490 |
| Example 5 | 50 | −80° C. | 510 | 480 | 500 |
| Example 6 | 50 | −80° C. | 510 | 520 | 490 |

Table 1: OSCN$^-$ in a Hydroalcoholic Solution

Example 7

Solid OSCN$^-$ Sodium Salt Obtained by Lyophilization

The frozen hydroalcoholic solution of Example 3 is lyophilized. A yield of 0.1% or 0.4 μg of Na OSCN$^-$ salt is obtained.

Example 8

Solid OSCN$^-$ Sodium Salt Obtained by Evaporation of the Solvents

A solution obtained according to Example 1 ([OSCN$^-$]= 617 μmol.l-1) is diluted with absolute ethanol (EtOH/H$_2$O of 9:1). The solvent is then evaporated in the form of an azeotrope at reduced pressure using a rotating evaporator (bath temperature of 40° C.) until the solvents are fully evaporated. The product obtained is a white powder.

The OSCN$^-$ content is checked by TNB colorimetric test (Ellman reagent).

20 μg of OSCN$^-$ is obtained, this being a yield of 21%.

Example 9

Solid OSCN$^-$ Sodium Salt Obtained by Evaporation of the Solvents

A solution obtained according to example 1 ([OSCN$^-$]= 1340 μmol.l-1) is diluted with absolute ethanol (EtOH/H$_2$O of 9:1). The solvent is then evaporated in the form of an azeotrope at reduced pressure using a rotating evaporator (bath temperature of 40° C.) until the solvents are fully evaporated. The product obtained is a white powder.

The OSCN$^-$ content is checked by TNB colorimetric test (Ellman reagent).

100 μg of OSCN$^-$ is obtained, this being a yield of 51%.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A solid composition comprising at least one hypothiocyanite salt (OSCN⁻) of a cation in an amorphous and/or crystalline powder form.

2. The composition according to claim 1, wherein the percentage by weight of the hypothiocyanite salt (OSCN⁻) of a cation falls within 0.01 and 10%.

3. The composition according to claim 1, further comprising a thiocyanate ion salt (SNC⁻) in a percentage by weight that falls within 0.1% and 10%.

4. The composition according to claim 1, further comprising gluconic acid in a percentage by weight that falls within 0.01% and 10%.

5. The composition according to claim 1, further comprising a phosphate or carbonate salt of an alkaline cation in a percentage by weight that falls within 10% and 99.9%.

6. The composition according to claim 1, further comprising glucose.

7. The composition according to claim 1, wherein the cation is an alkaline cation.

8. The composition according to claim 7, wherein the alkaline cation is a sodium or potassium cation.

9. The composition according to claim 1, wherein the cation is a calcium or magnesium cation.

10. A hydroalcoholic solution comprising a composition according to claim 1, wherein alcohol is present is an amount between 0.01% and 100% by weight of solvent.

11. The solution according to claim 10, wherein the alcohol is selected from the group consisting of ethanol, polyethylene glycol, tert-butanol and a compound carrying hydroxyl functions.

12. The solution according to claim 11, wherein the compound carrying hydroxyl functions is selected from the group consisting of mannitol, trehalose and lactose.

13. The solution according to claim 11, wherein the alcohol is ethanol in a percentage by weight comprised between 10 and 99.9%.

14. A process for obtaining a composition according to claim 1, the process comprising:

a) adding between 10 and 99.9% by weight of at least one alcohol to an aqueous solution containing at least a hypothiocyanite ion (OSCN⁻), wherein, the alcohol is a dissolved solid or a solvent;
   b) setting a temperature of the solution from step a) to between 0° C. and −100° C;
   c) removing solvent;
   d) obtaining a solid composition of claim 1.

15. The process according to claim 14, wherein the alcohol is selected from the group consisting of ethanol, polyethylene glycol, tert-butanol and a compound carrying hydroxyl functions.

16. The process according to claim 15, wherein the compound carrying hydroxyl functions is selected from the group consisting of mannitol, trehalose and lactose.

17. The process according to claim 15, wherein an association of at least two alcohols are added to the aqueous solution.

18. The process according to claim 15, wherein the alcohol is ethanol in a proportion by weight ranging between 0.01 and 50%.

19. The process according to claim 14, wherein the solvents are removed simultaneously.

20. The process according to claim 14, wherein the solvents are removed consecutively.

21. The process according to claim 14, wherein the solvents are removed by evaporation in the form of an azeotrope at reduced pressure.

22. The process according to claim 14, further comprising before step a), a step x) for producing the aqueous solution containing at least the hypothiocyanite ion (OSCN⁻) by placing in contact a peroxidase, a pseudohalogen and an oxygen donor.

23. A method for treating an airborne infection, a lower respiratory tract infection or an upper respiratory tract infection in a subject in need thereof, the method comprising administering to the subject a therapeutically effective amount of a composition according to claim 1.

24. The method according to claim 23, wherein the composition according to claim 1 is administered in combination with another antimicrobial, preservative or antibiotic agent.

* * * * *